US008112139B2

(12) United States Patent
Sun et al.

(10) Patent No.: US 8,112,139 B2
(45) Date of Patent: Feb. 7, 2012

(54) SKIN SCREW ELECTRODE

(75) Inventors: Mingui Sun, Pittsburgh, PA (US);
Robert J. Sclabassi, Gibsonia, PA (US);
Wei Liang, Zhengzhou (CN); Joseph Marcanio, Greensburg, PA (US)

(73) Assignee: University of Pittsburgh—of the Commonwealth System of Higher Education, Pittsburgh, PA (US)

(*) Notice: Subject to any disclaimer, the term of this patent is extended or adjusted under 35 U.S.C. 154(b) by 1025 days.

(21) Appl. No.: 12/012,607

(22) Filed: Feb. 4, 2008

(65) Prior Publication Data
US 2008/0262335 A1 Oct. 23, 2008

Related U.S. Application Data

(60) Provisional application No. 60/887,879, filed on Feb. 2, 2007.

(51) Int. Cl.
*A61B 5/0478* (2006.01)
(52) U.S. Cl. ......... 600/382; 600/383; 600/377; 600/544
(58) Field of Classification Search .................. 600/377, 600/382, 383, 393, 509, 544, 378
See application file for complete search history.

(56) References Cited

U.S. PATENT DOCUMENTS

| | | | | |
|---|---|---|---|---|
| 4,653,503 A | * | 3/1987 | Heath | 600/391 |
| 4,936,306 A | * | 6/1990 | Doty | 600/373 |
| 5,003,978 A | | 4/1991 | Dunseath, Jr. | |
| 5,511,553 A | * | 4/1996 | Segalowitz | 600/508 |
| 6,175,753 B1 | | 1/2001 | Menkes et al. | |
| 6,201,982 B1 | | 3/2001 | Menkes et al. | |
| 6,438,413 B1 | | 8/2002 | Taheri | |
| 6,491,647 B1 | | 12/2002 | Bridger et al. | |
| 6,690,959 B2 | | 2/2004 | Thompson | |
| 6,782,283 B2 | | 8/2004 | Schmidt et al. | |

(Continued)

FOREIGN PATENT DOCUMENTS
DE 3446116 A1 * 6/1986

OTHER PUBLICATIONS

Griss, P., et al., "Characterization of Micromachined Spiked Biopotential Electrodes", IEEE Transactions on Biomedical Engineering, vol. 49, No. 6, Jun. 2002.

(Continued)

*Primary Examiner* — Lee Cohen
*Assistant Examiner* — Erin M Cardinal
(74) *Attorney, Agent, or Firm* — Reed Smith LLP

(57) ABSTRACT

Electrodes providing excellent recording and physical stability. Electrodes that include a plurality of small teeth that possess a novel design shape and orientation are disclosed. The shallow and relatively long teeth preferably run parallel to the rim of the electrode that presses against the patient's skin. When the electrode is twisted onto skin, the teeth penetrate nearly horizontally under the stratum corneum. The electrodes cause minimal discomfort to the patient since the teeth do not extend to the pain fibers which are located in deeper layers of the skin. The electrodes may house a diversity of electronic components to enable numerous experimental and medical implementations. The electrodes may also be used wirelessly without electrode leads. The electrodes may be fabricated using precision photo-chemical etching techniques that are well known in the art. An electrode installation device that preferably employs the electrodes is also disclosed.

18 Claims, 7 Drawing Sheets

U.S. PATENT DOCUMENTS

| | | |
|---|---|---|
| 7,032,301 B1 | 4/2006 | Schmidt et al. |
| 7,397,364 B2 | 7/2008 | Govari |
| 2005/0145491 A1 | 7/2005 | Amano et al. |
| 2006/0074336 A1 | 4/2006 | Grieve et al. |
| 2006/0293723 A1 | 12/2006 | Whitehurst et al. |
| 2007/0015984 A1 | 1/2007 | Yeo et al. |
| 2007/0225585 A1* | 9/2007 | Washbon et al. ............ 600/393 |

OTHER PUBLICATIONS

Ruffini, G. et al., "A Dry Electrophysiology Electrode Using CNT Arrays", Physics (on-line journal), Paper No. 0510145, Apr. 6, 2006.

Griss, P, et al., "Micromachined Electrodes for Biopotential Measurements", Journal of Microelectromechanical Systems, vol. 10, No. 1, Mar. 2001.

* cited by examiner

SKIN SCREW ELECTRODE

CROSS-REFERENCE TO RELATED APPLICATION

This application claims the benefit under 35 U.S.C. §119 (e) of the earlier filing date of U.S. Provisional Application Ser. No. 60/887,879 filed on Feb. 2, 2007.

GOVERNMENT SUPPORT STATEMENT

This invention was made with government support under Contract No. R41/R42 NS36888 awarded by the National Institutes of Health. The government has certain rights in this invention.

BACKGROUND OF THE INVENTION

1. Field of the Invention

The present invention relates to electrodes that are adapted for fast installation and stable implantation into the skin of a subject. The electrodes are useful for a variety of physiological recording and stimulation applications.

2. Description of the Background

The electrical nature of physiological processes has been known for over a century. The electrical components of neuronal activity and the contraction of muscles may be recorded using electrodes placed onto the surface or just below the surface of the skin. Furthermore, excitable tissues, such as nerves and muscles, may be stimulated electrically to achieve various physiological effects.

The electroencephalogram (EEG), as a commonly-utilized diagnostic tool, provides a unique window to observe the functional activity within the brain. Recent technological advances in electronic and computer systems have allowed over one-hundred EEG channels to be recorded simultaneously and modern signal and data processing techniques have provided new insights into the recorded data, both in the temporal and spatial domains. Similar advances have affected the techniques used to record other electrophysiological events in the body, such as electromyograhy (EMG).

Recording of electrophysiological events in the body may be useful in diagnosing a variety of physiological disorders. For example, EEG allows for the non-invasive measurement of the electrical activity of the brain to diagnose epilepsy, sleep disorders, or determine the state of the brain during coma. By assessing the entry of a patient into a sleep state, EEG may also be used to maintain a state of arousal in a patient. EEG in the form of event related potentials (ERPs) is also commonly used in clinical neurophysiology to evaluate the functional or cognitive response of the central nervous system to a certain stimulus. Finally, EEG is currently being employed as part of systems that establish an interface between the brain and an external device—so called brain-computer interfaces.

Despite the recent technological advances and the large number of potential applications, affixing EEG recording electrodes onto the scalp of a subject requires a manual procedure which is a long, difficult process for both the EEG technician as well as the subject. Hair on skin will hinder the ability of the electrode to adhere to the patient. Because of body heat drying the electrolytic gel, the electrode impedance will increase over time. In addition, due to body motion, snagging of the wire leads, and deterioration of the adhesive, electrodes will often fall off. In light of these difficulties, the labor and facility usage costs for electrode installation have been a significant portion of the total cost of clinical EEG studies and have significantly hindered the acceptance of large-array EEG in clinical applications. In addition, some applications require improved electrical access that may be obtained chiefly through the insertion of needle electrodes under the skin. The insertion may be quite painful for the patient and is accompanied by a variety of concerns regarding the safety of the patient.

An additional difficulty encountered during EEG is in the stability of electrode attachment to the body. The electrode is connected to a wire lead which in turn runs to the signal recording device. Because of the natural movements of the patient, the wire leads will often become tangled and pulled by the patient. The electrode will subsequently be pulled off of the skin and require reattachment. The wire leads of common EEG electrodes can also act as tethers which limit the movement of the patient, which in turn limits the potential application of EEG and EMG.

Prior work has attempted to address some of the deficiencies of EEG electrodes. For example, U.S. Pat. Nos. 6,175,753 and 6,201,982 to Menkes et al. discloses quick-placement EEG electrodes. The electrodes disclosed in those patents attempt to avoid the problems associated with hair on the patient by actually attaching the electrode to the hair of the patient, thereby stabilizing the electrode. The electrodes disclosed by Menkes et al. also include a sponge that replenishes the electrolytic gel for prolonged applications. Nevertheless, the electrodes would still suffer from some of the shortcomings of the prior art, including inconsistent electrical contact with the skin due to eventual drying of the electrolyte solutions, physical instability of the electrode, and clinical feasibility of allowing a large number of electrodes to be affixed to the scalp rapidly.

Thus, there has been a long-standing need for electrodes that may be quickly and securely placed on a patient without requiring shaving of the skin or administration of adhesive. In addition, typical electrode administration often employs an abrasion step where a layer of the skin is worn off to improve the signal. Such procedures are time consuming and are often uncomfortable for the patient. The electrodes would preferably be stable after implantation and provide excellent electrical contact to the skin for both recording and stimulation of the tissue in the area of the electrode, with or without the use of electrolytic gels.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

SUMMARY OF THE INVENTION

Figure 1:
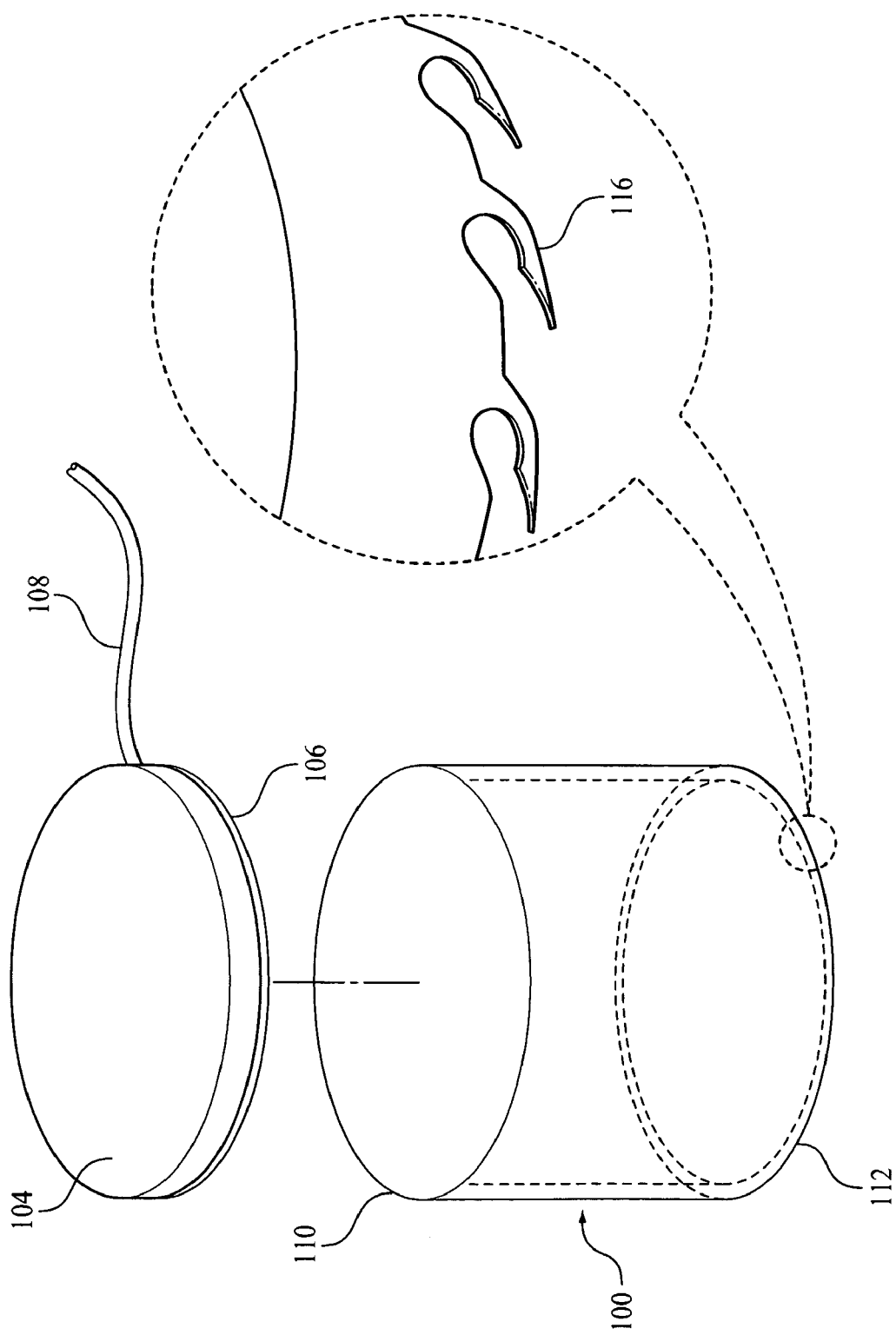
FIG. 1 displays a schematic of a presently-preferred embodiment of the present invention.

The present invention is directed to recording and stimulating electrodes that are easily and stably attached to the skin. The present invention provides a simple, effective, and low-cost design that solves many of the traditional problems associated with the installation of an electrode onto the hairy skin of human and animal patients. The electrodes of the present invention preferably include small teeth that possess a novel design shape and orientation. The teeth reside along the rim of a cylindrical electrode that comes in contact with the patient's skin. The plurality of shallow and relatively long teeth preferably runs parallel to the rim of the electrode. When the electrode is twisted onto skin, the tiny teeth penetrate the stratum corneum and move nearly horizontally with respect to the skin surface under the stratum corneum, thus anchoring the electrode securely to the skin. As such, the electrodes of the present invention preferably do not cause pain because the small teeth do not extend to the pain fibers which are located in a deeper layer of the skin, yet the electrodes provide for excellent electrical access to the interior of the body as well as tremendous physical stability.

Because of their superior physical stability, the electrodes of the present invention are well suited to house electronic components that may accomplish a wide variety of tasks. For example, the electrodes of the present invention may include sensors designed to measure blood oxygenation, blood glucose levels, or other common physiological variables. The electrodes the present invention may also be used wirelessly either singularly or as an array so that no electrode leads extend away from the patients body, thereby reducing the annoyance of the electrode assembly for the patient. That implementation of the present invention is particularly appropriate for situations where numerous electrodes are commonly used, such as EEG or EMG recordings.

The electrodes of the present invention may be fabricated either as a single integrated unit or as a multi-component system depending on the specific demands of the application. In certain presently preferred embodiments, the electrodes of the present invention may be fabricated using precision photo-chemical etching techniques that are well known in the art. The present invention also includes an electrode installation device that preferably employs the electrodes of the present invention.

DETAILED DESCRIPTION OF THE INVENTION

It is to be understood that the figures and descriptions of the present invention have been simplified to illustrate elements that are relevant for a clear understanding of the invention, while eliminating, for purposes of clarity, other elements that may be well known. The detailed description will be provided hereinbelow with reference to the attached drawings.

The present invention provides electrodes that may be quickly and stably attached to a patient. The electrodes of the present invention do not require any pre-treatment of the skin to be applied and as such represent a significant improvement over the prior art. In addition, the electrodes of the present invention may be applied to hairy skin (e.g., scalp) of a patient. Insofar as the present invention may have general applicability, as used herein, "patient" refers to both human and animal subjects who either have a medical condition or are healthy. The electrodes of the present invention provide superior physical stability and electrical access to the skin of the patient, thus representing a significant improvement over the prior art. The electrodes of the present invention may be employed both as stimulating electrodes and recording electrodes as detailed hereinbelow.

The general structure of an electrode 100 of the present invention is shown in FIG. 1. The electrode 100 is generally cylindrical in shape with a hollow interior that is capable of housing electronic components as described further hereinbelow. The electrodes 100 may include a magnetic cap 104 attached to a brass plate 106 from which an electrical lead 108 extends. The magnetic cap 104 may attach to the distal rim 110 (i.e., the portion of the electrode that is away from the skin of the patient) of the electrode, thus forming the outside portion of the chamber within the body of the electrode. The electrodes 100 preferably have a diameter of about 10 millimeter for easy handling; however, the diameter may vary considerably depending on specific applications. The proximal rim 112 of the electrode (i.e., the portion of the electrode that rests against the skin of the patient) includes a plurality of teeth 116 (shown at higher resolution in FIG. 2) that extend therefrom.

Figure 2:
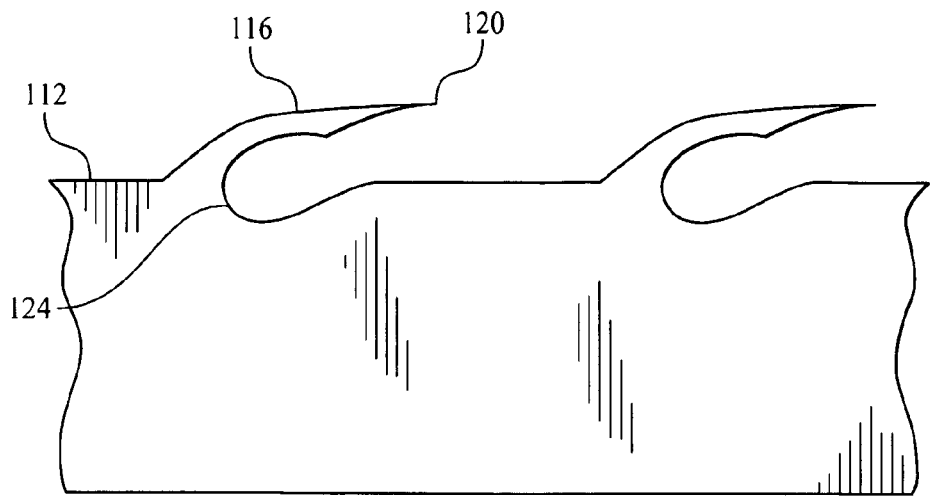
FIG. 2 is a close-up view of the teeth of the electrodes of the present invention.

A higher resolution of the proximal rim of the present invention is shown in FIG. 2. The teeth 116 run parallel to the proximal rim of the electrode though the specific geometry of the teeth may vary widely. The teeth 116 preferably extend between 0.002 inches and 0.005 inches from the proximal rim 112 of the electrode. The teeth 116 are preferably oriented from about 2° to about 5° away from the rim 112. The teeth 116 preferably have a sharp tip 120 that allows for easy penetration of the epidermis. The length of the teeth may vary widely depending on the particular implementation, with presently preferred embodiments having a length of about 0.005 inches to about 0.05 inches with a length of about 0.01 inches being presently preferred.

As seen in FIG. 2, at the base of the teeth 116 a small recessed area 124 is formed. This recessed area 124 is well suited to capture any hair that may be present on the surface of the patient's skin. A wide variety of shapes for the recessed area 124 may be used depending on the particular application where the electrodes are employed. By employing this configuration, the electrodes 100 of the present invention are secured to the surface of the skin regardless of the presence of the hair. The electrodes 100 of the present invention thus avoid any need for manually paring the hair prior to placement of the electrodes.

The teeth 116 are preferably of a length and angle such that they are capable of penetrating the epidermis to just past the level of the stratum corneum. The specific length, shape and angle of the teeth of the electrodes of the present invention may be varied widely, with embodiments where the teeth penetrate the epidermis past the stratum corneum, though not to the level of pain fibers being particularly preferred. By being oriented at such a slight angle from the rim of the electrode 112, the penetration depth of the electrodes 100 of the present invention is limited, thereby drastically reducing discomfort for the patient. At the same time, the plurality of teeth 116 forms a sturdy attachment to the skin through the interaction with the stratum corneum.

Figure 3:
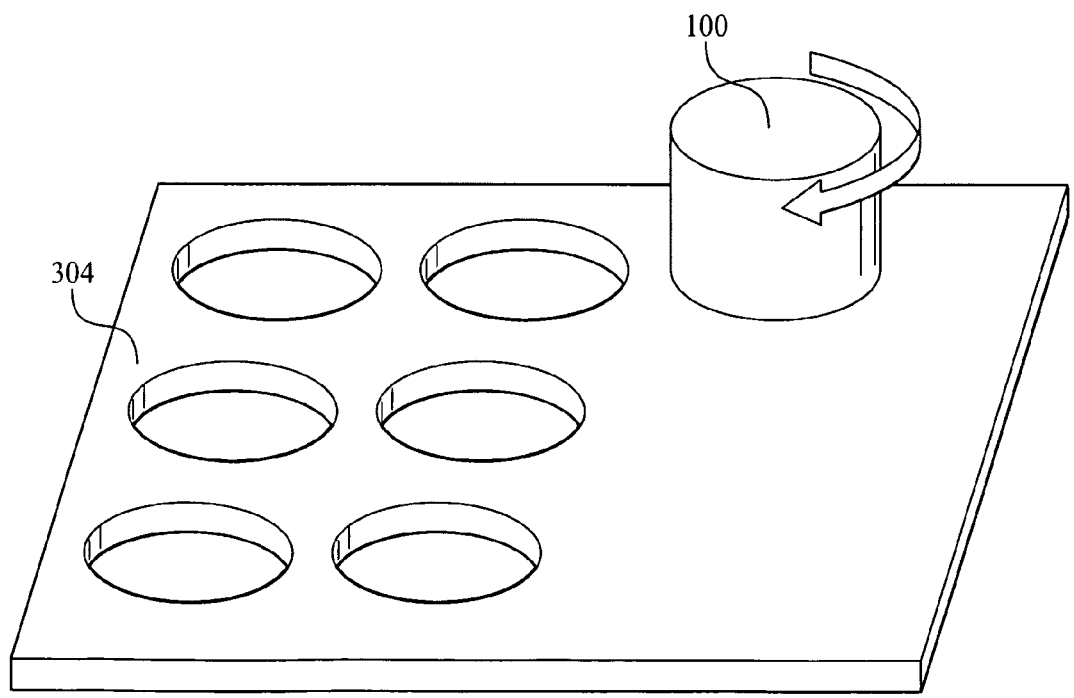
FIG. 3 depicts how an electrode of the present invention may be used with an electrolyte-containing hydrogel.

By piercing the stratum corneum and reaching the water-containing portions of the epidermis below, the electrodes of the present invention also provide excellent electrical access to the patient with electrode impedance on the order of 5 k$\Omega$ being commonly observed without use of any electrolytic gels. The electrodes of the present invention may also be used with electrolytic gels to improve impedance as the particular situation warrants. In those instances where an electrolytic gel is used, the electrodes 100 of the present invention may be pressed and turned lightly into a sheet of hydrogel 304 that contains a certain amount of ionic electrolyte compound, as shown in FIG. 3.

The shape, size, and material properties of the teeth are substantive factors in the design of the electrodes of present invention. Since the teeth are preferably very small, the material at the rim of the electrode will be both sufficiently hard and stress resistant so that the teeth will not bend or break off during electrode installation. The use of stainless steel alloy is presently preferred in that it achieves an appropriate hardness after an annealing treatment. In certain presently-preferred embodiments, the steel alloy includes a sufficient amount of iron to achieve magnetic permissibility for lead wire connection as described below.

The electrodes may be fabricated from any well-known conductive material, with stainless steel, copper alloy, gold alloy, and platinum being presently preferred. However, any conductive substance, including metals, carbon products, and conductive polymers, could be employed to fabricate the electrodes of the present invention. In order to improve performance, the electrode teeth may be coated or electroplated with a material of low half-cell potential (e.g., silver-silver chloride), an anti-oxidation metal (e.g., gold), or a high electron-transfer material (e.g., iridium). The electrodes may be fabricated as a single unit made entirely from one type of material. In other presently preferred embodiments described below, the electrodes may be made of multiple components including plastic or other non-conductive materials. The teeth of the electrode may include nickel, which is a common component of stainless steel. To reduce the likelihood or severity of reactions in patients who are allergic to nickel, the teeth of the electrodes of the present invention may be coated with a metal or conductive metal oxide. The electrodes of the present invention may be synthesized from a material that is either disposable or autoclavable, thus eliminating cross-infection potential in human applications.

In presently-preferred embodiments of the present invention, the electrodes possess the approximate external dimensions of prior art EEG electrodes (on the order of 1 centimeter). However, alternative dimensions that are tailored to the specific application may also be employed. For example, if electrodes are to be used on a small patch of skin, a small animal, or applied using an automatic tool, the diameter of the electrode could be reduced.

Figure 4:
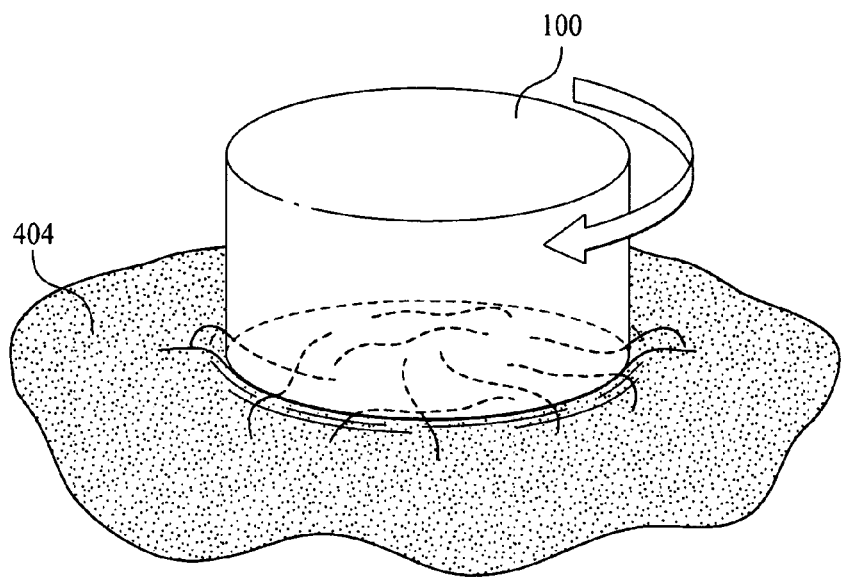
FIG. 4 shows how a presently-preferred embodiment of the present invention may be attached to the body of a patient.

The application of the electrode 100 to a patient's skin is preferably made by slightly pressing towards the body while turning the electrode clockwise as shown in FIG. 4. Accordingly, the electrode 100 is quickly and firmly affixed to the skin of the patient 404. The application of the electrode 100 typically causes no pain since the depth of penetration is not sufficient to reach the pain receptors located in the deeper portions of the skin. After the electrode is applied to the patient, all of the teeth are preferably extended nearly horizontally under the stratum corneum resulting in a large total electrical contact area and a secure attachment to the skin.

In many prior art electrodes, the electrode lead is permanently connected to the electrode. As the number of electrodes installed on the scalp, for example, increases, the space above the head becomes cluttered with wires. In addition, when an electrode lead is accidentally pulled, the electrodes may separate from the scalp requiring a compete re-installation. The present invention preferably overcomes these limitations. In certain presently-preferred embodiments, a magnetic disk 104 glued to a brass plate 106 makes electrical contact between the wire lead 108 (which may be soldered to the brass plate 106) and the electrode 100 as shown in FIG. 1. As such, in the present design magnetic attraction is preferably used to connect electrodes 100 to the wire leads 108. This innovation provides a number of advantages: 1) electrodes can be easily separated from the leads, making their use convenient for the patient (e.g., for taking a shower or leaving the recording room temporarily); 2) it further facilitates the use of a hand-held installation devices, as described below; and 3) when any electrode lead is accidentally pulled, only the magnetically-connected lead will separate and the electrode placement on the patient's skin would not be disturbed. In other presently-preferred embodiments, the electrode may be fabricated from materials that are not magnetic. In those embodiments, the wire lead may be reversibly attached to the electrode in a variety of manners, such as adhesive, snap joints, or other methods commonly known in the art.

Figure 5:
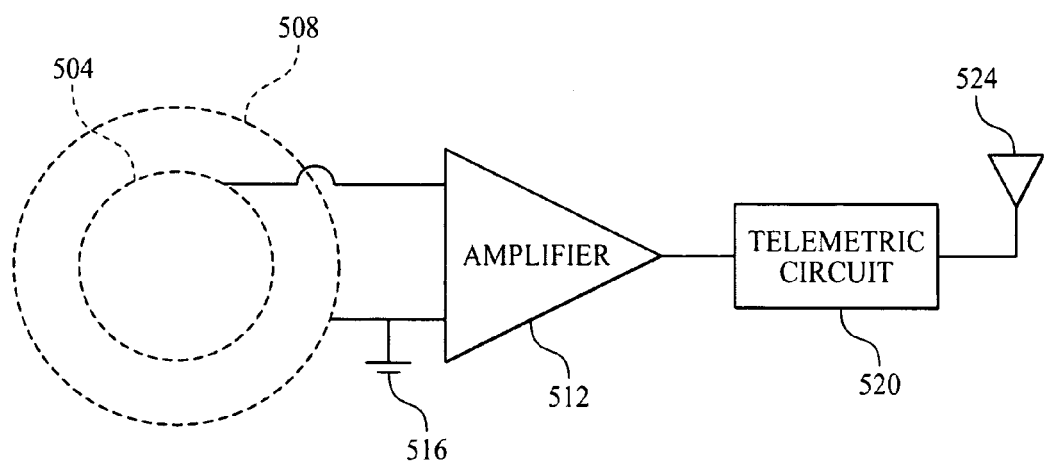
FIG. 5 is schematic for a wireless implementation using a single electrode of the present invention.

Since the presently-preferred electrode design of the present invention provides an electrically-shielded space inside the electrode, electronic circuits may be placed within this space, converting the passive electrode into an active device. A particular implementation of this principle is to employ two electrically-insulated rims of teeth 504, 508 to acquire a bipolar signal from the body as shown in FIG. 5. The signal may be amplified through an amplifier 512 within the interior of the electrode where the outer rim 508 is grounded 516, thus providing an ideal shield from exterior interference. The interior space may also contain a small battery and a telemetric circuit 520 (e.g., RF, infrared, or BLUETOOTH), providing power and transmitting 524 a single channel to a nearby receiver (e.g., a cell phone, PDA, or receiver attached to a recording device).

While the implementation of the present invention shown in FIG. 5 is for recording an electrical signal of relatively large amplitude, the electrodes of the present invention, when equipped with the appropriate electronic components, may also act as stimulating electrodes. As a stimulating electrode, the present invention could be used in a wide variety of situations to deliver small currents to underlying tissues. For example, prior art techniques such as transcutaneous electrical nerve stimulation (TENS) and percutaneous electrical nerve stimulation (PENS) have been used to treat chronic pain that is not responsive to other treatments. The electrodes of the present invention provide a tremendous tool for use in these applications and may be modified for use in those areas by the inclusion of well-known electronic components and circuitry.

Figure 6A:
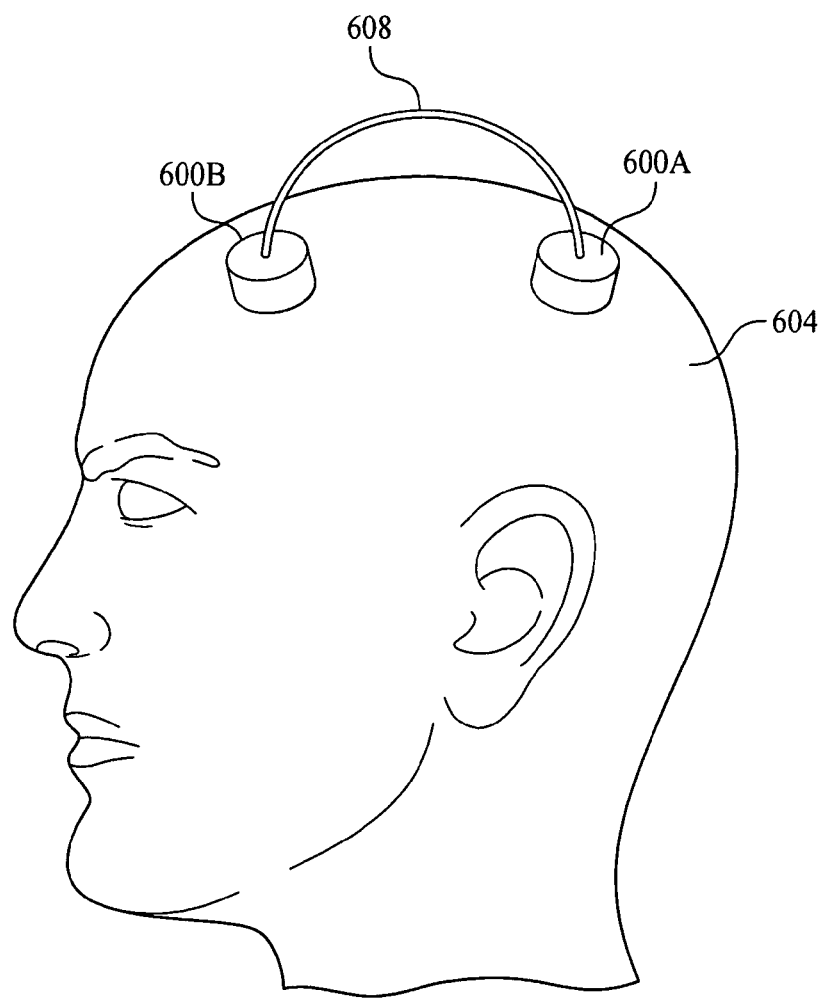
FIG. 6 shows multiple configurations of electrodes of the present invention that may be used in recording from a patient.

The electrodes of the present invention may also be used in arrays of two or more to create ultra-portable, wireless recording devices capable of high fidelity collection and transmission of data. As shown in FIG. 6A, two electrodes 600A, 600B may be applied to the scalp of a patient 604 with a cable 608 connecting the two electrodes 600A, 600B. In that configuration, the cable 608 may communicate data and power between electrodes 600A, 600B while at the same time acting as an RF antenna. In certain preferred embodiments, the cable 608 may be shielded, with the shield acting as the antenna for data transmission and reception. The antenna could be used to transmit the amplified EEG signal to a nearby computer or receiving station using any standard protocol such as BLUETOOTH.

Figure 6B:
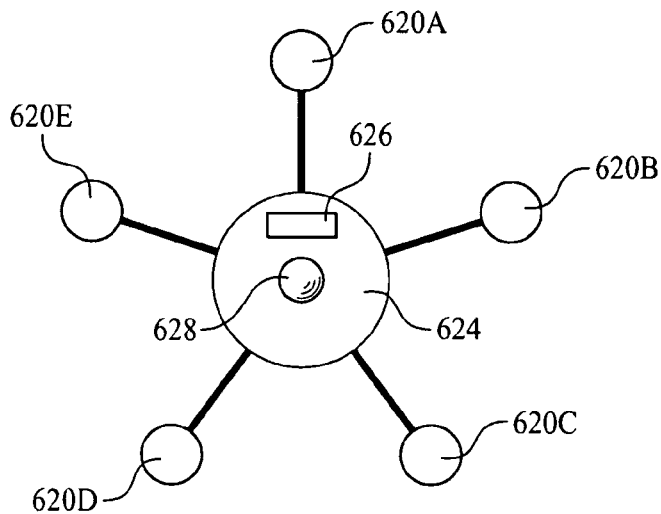
Figure 6C:
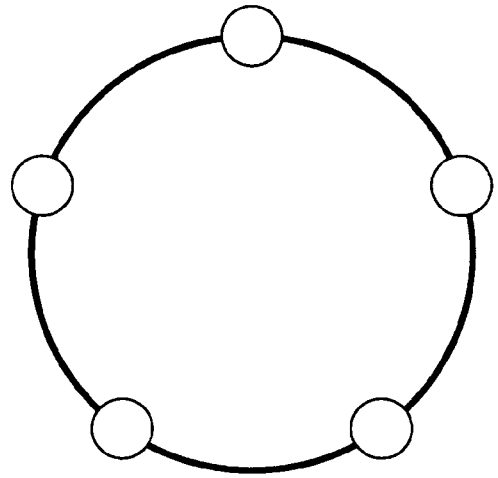
Figure 6D:
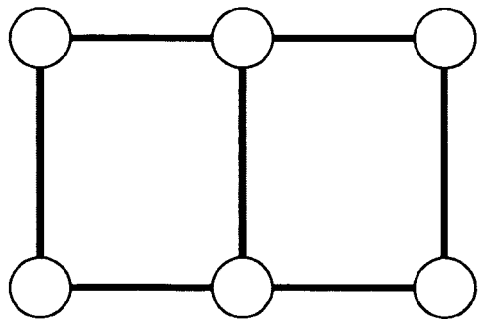

In other present preferred configurations, electrodes 620 could be placed in a star pattern (FIG. 6B) with a central unit 624 that may connect to the patient using the same small teeth as the electrodes 620. The central unit 624 can be either an electrode or a non-electrode, including electronic components such as a switch to turn on or off the device or a gain control 626. The central unit 624 may also include an infrared light emitter 628 for the telemetric transmission of data. Multiple electrodes may also be placed in a loop (FIG. 6C) or a net (FIG. 6D) configuration. By using multiple electrodes, the number of channels of data that are recorded simultaneously may be increased. One of skill in the art will recognize a wide variety of configurations that may be employed depending on the physiological data that is to be collected (e.g. EEG, EMG, or EKG).

Figure 7:
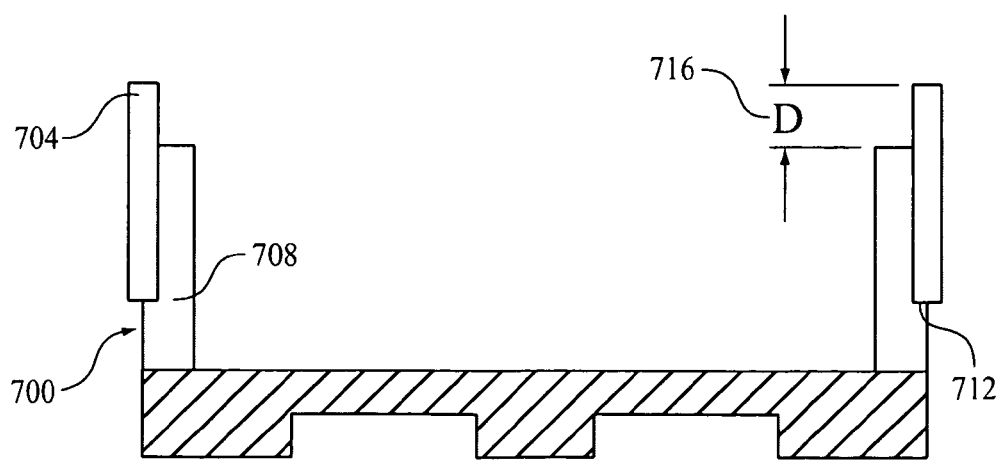
FIG. 7 depicts a cut-away view of a multi-component electrode design of the present invention.

As indicated above, the body of the electrodes of the present invention may be fabricated as a single integrated unit made of one conductive material. In other presently preferred embodiments, the electrodes are constructed of multiple components with such configurations providing a simple manner for the large-scale manufacture of the electrodes. A side-view of the multi-component embodiment of the electrode 700 shown in FIG. 7 contains an electrode rim 704 that includes the electrode teeth as described hereinabove and a constraining wall 708 which makes up the remainder of the electrode body. Both the constraining wall 708 and the electrode rim 704 that includes the electrode teeth are cylinders. The constraining wall 708 has an alignment notch 712 along its exterior face. The depth of the alignment notch 712 is set so that the maximum penetrating depth of the electrode teeth is set to depth D 716, as shown. The constraining wall 708 may be fabricated from either metal or plastic as described further hereinbelow. In this configuration the rim of the electrode that includes the electrode teeth 704 fits tightly over the constraining wall 708 such that the two form an integrated electrode body 700.

Figure 8A:
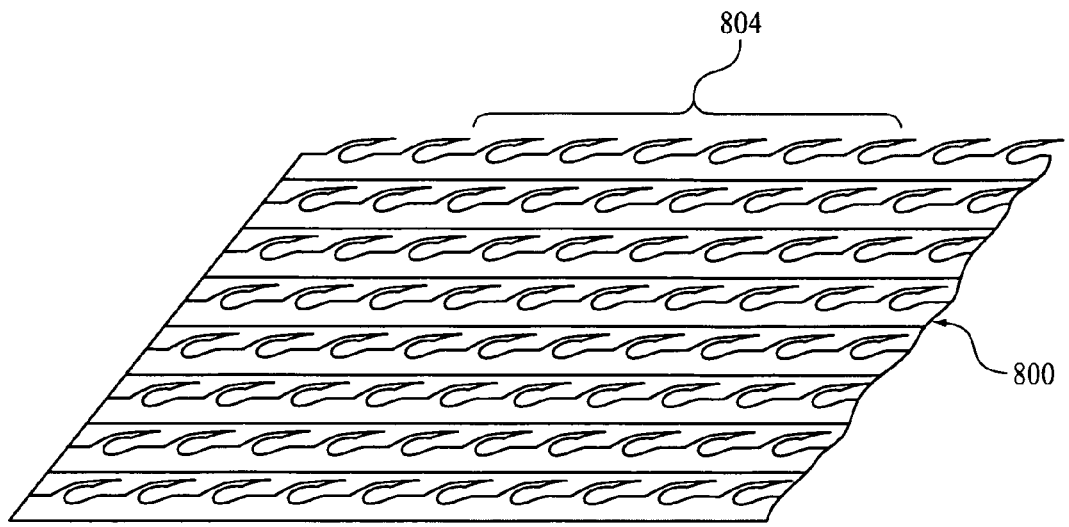
FIG. 8 shows a step in a presently preferred method for making the electrodes of the present invention.
Figure 8B:
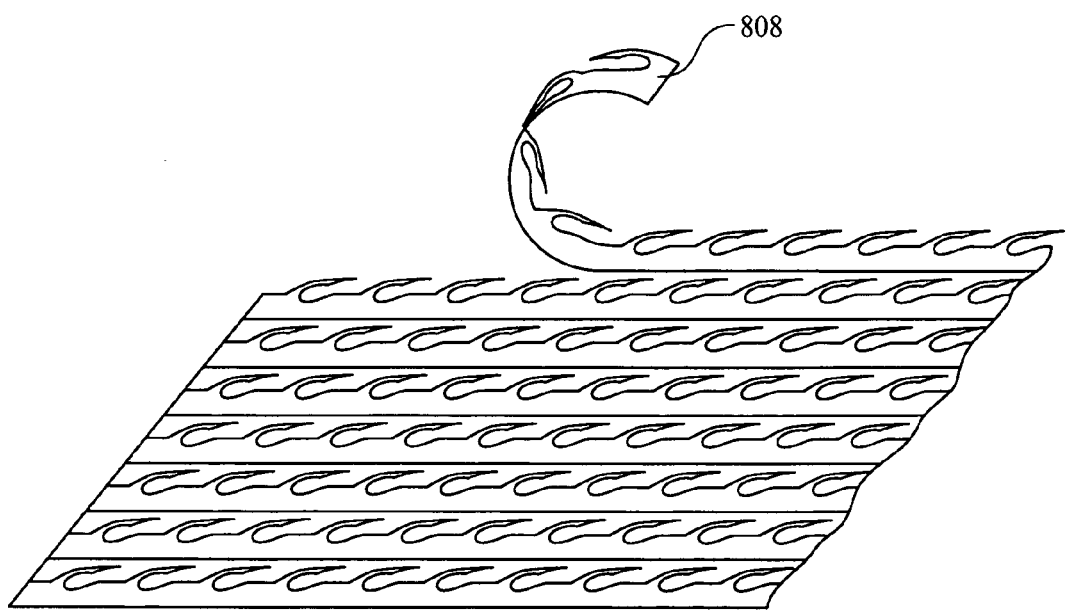

The electrode rim that includes the electrode teeth 704 may be fabricated using the commonly known technique of photochemical etching (or photochemical milling). The repeating pattern of teeth 804 (as also shown in FIG. 2) may be printed as an etchant-resistant chemical onto both sides of a sheet of metal 800, e.g. stainless steel. The pattern 804 would preferably have the design of the opened electrode cylinder. The pattern 804 could be repeated multiple times on the same sheet of metal 800, such as shown in FIG. 8A. After the etchant-resistant chemical dries, the metal is exposed to the etching reagent and those portions which are not protected by the etchant-resistant chemical are eroded. The remaining metallic strip 808 is in the shape of the proximal rim of the open electrode cylinder including the electrode teeth. The metallic strip 808 may then be closed and fused using well-known techniques, such as tack welding, to form the cylindrical electrode body. The metallic strip 808 may be formed into a cylinder around the constraining wall (FIG. 7) to ensure a tight fit between the two components and so that the depth of the electrode teeth may be set appropriately.

In other present preferred embodiments, the constraining wall may be formed from a plastic mold. In those embodiments, the metallic strip may include holes in the body of the strip where plastic could flow during molding, thereby forming a strong connection between the two components once the plastic dries. One of skill in the art will recognize variations of these methods for the fabrication of the electrodes of the present invention, such as negative etching or standard high-precision machining.

Although the electrodes of the present invention may be applied manually, in cases where a large number of electrodes need to be installed, the electrode technician might hand-pick individual electrodes from a container which takes a significant amount of time. In addition, it is often desirable to know the exact coordinates of the electrodes on the patient's body (e.g., scalp) relative to a known reference point. Although these coordinates can be acquired using a Polhemus sensor, such processes are time consuming for the administration of a large number of electrodes. In order to address these issues, the present invention may also include a "volley gun"-like electrode installation device. Since the electrodes of the present invention preferably have no leads prior to installation, a pack of electrodes of identical size may be loaded into the electrode installation device, greatly reducing the time between electrode installations. The electrode installation device may also be equipped with a coordinate sensor, e.g., similar to a Polhemus sensor, to record the coordinates of each electrode as it is installed on the patient's skin, taking little extra time during operation.

Figure 9:
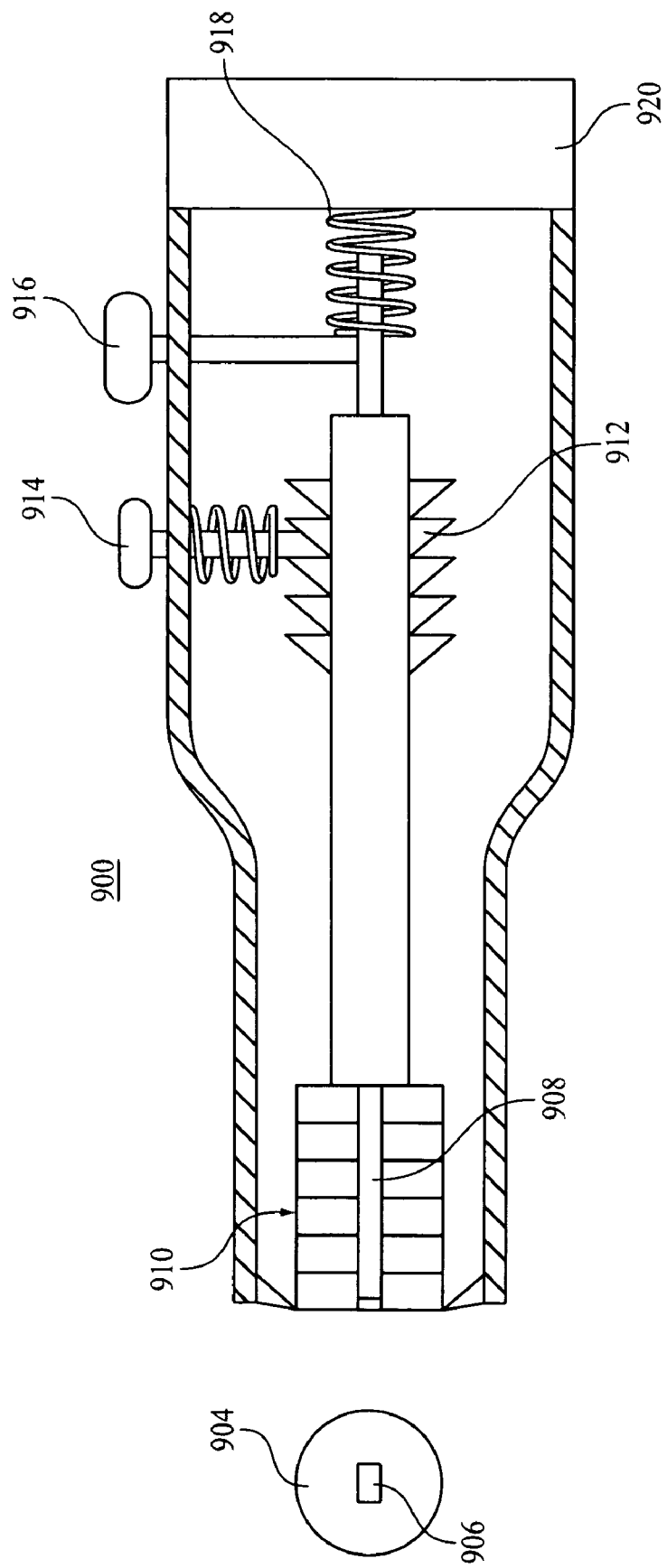
FIG. 9 displays a schematic of an electrode installation device of the present invention.

A presently-preferred structure of the electrode installation device 900 is shown in FIG. 9. In this embodiment, the electrode 904 has a non-circular (e.g., square or hexagonal) central hole 906 that allows the electrode to be twisted by a rod 908. A pack of electrodes 910 is stepped forward by a stepping assembly preferably containing a gear 912, and buttons 914 and 916. A spring 918 may be utilized to load the next electrode automatically. A position sensor 920, which may contain a radio frequency (RF) circuit, measures electrode location and transmits the result (either wirelessly or via a wire) to a computer after each electrode installation.

The electrodes of the present invention may be used for various physiological recording techniques such as traditional EEG, EKG, EMG, and other electrophysiological applications. The present invention may also be used in other applications where the device is not used as an electrode. Because of the strength with which the electrodes may be attached to the skin, they may be used to anchor another device onto the skin more securely than by employing standard adhesive tape. For example, when equipped with the appropriate electronic components, the electrodes of the present invention may be used to assess a variety of additional physiological measures such as blood oxygenation and blood glucose levels. With a leak-preventive seal, a liquid-form drug may be stored within the chamber of the device and delivered transcutaneously. Drug delivery may also benefit from electronically scheduled and controlled electroporation in which a transcutaneous current is utilized to open microscopic channels through which drug may be delivered through the skin in a desired amount.

The electrodes of the present invention may also be used to stimulate muscle tissue. Microcurrent stimulation of muscles may be employed to treat age-related macular degeneration, wound healing, tendon repair, and ruptured ligament recovery. Further, the present invention may be used to stimulate muscle to improve their strength such as in patients suffering from osteoarthritis or to preserve muscle tone and mass during extended periods of disuse such as coma or surgery recovery. Electric simulation of muscles may be utilized to mimic the effect of exercise in weight management and treatment of obesity.

The electrodes of the present invention may be connected to a variety of electronic components to enable a diversity of technical and medical implementations. Examples include: 1) a game system controlled by the brain waves of the player, where those brain waves are measured using electrodes of the present invention; 2) a robotic system that serves a paralyzed patient by employing measurements of patients' EEG and EMG signals assessed through the electrodes of the present invention; 3) an ambulatory EEG recorder employing electrodes of the present invention for emergency medical care; and 4) an automatic drowsiness monitor for motor vehicle drivers. The wireless design of the present invention greatly facilitates a number of specialized experimental applications, such as unconstrained neurophysiological monitoring during behavior, where it is preferably for animal or human subjects to have free range of motion within an environment.

Those of skill in the art will recognize that numerous modifications of the above-described process can be performed without departing from the present invention. For example, modification of the specific geometry of the teeth of the electrodes and variation of the electronic components coupled to the present invention are considered to be within the scope of the present invention.

We claim:

1. An electrode for attachment to skin of a patient comprising:
   an electrode body, wherein said electrode body is a cylinder having a vertical wall with a first rim at a top of said cylinder and a second rim at a bottom of said cylinder, said first rim of said cylinder having a plurality of teeth, wherein each tooth includes a shaft that initially extends vertically from said first rim and then turns to run roughly horizontally to said first rim within the vertical plane defined by the wall of said cylinder and;
   a cap that is connected to said second rim of said electrode body.

2. The electrode of claim 1, wherein said teeth are located around the entirety of said first rim.

3. The electrode of claim 1, wherein said shaft of said teeth are between about 0.005 and about 0.05 inches long.

4. The electrode of claim 1, wherein said teeth are adapted to penetrate the stratum corneum of said skin, but not as deep as the layer containing pain fibers.

5. The electrode of claim 1, wherein said teeth extend vertically from about 0.002" to about 0.005" from said first rim.

6. The electrode of claim 1, wherein said teeth are angled away from said first rim from about 2° to about 5°.

7. The electrode of claim 1, further comprising a recessed area in said first rim at a base of each of said plurality of said teeth, wherein each recessed area is adapted to accommodate any hair located on the surface of said skin.

8. The electrode of claim 1, wherein said electrode is fabricated from a conductive material selected from the group consisting of stainless steel, copper alloy, conductive polymer, gold alloy, and platinum.

9. The electrode of claim 1, wherein said teeth are electroplated or coated with a silver-silver chloride, gold, iridium, or conductive metal oxide.

10. The electrode of claim 1, wherein said electrode body and said cap are magnetic.

11. The electrode of claim 10, further comprising an electrical lead wire connected to said cap.

12. The electrode of claim 1, further comprising an amplifier, a telemetric circuit, and a transmitter.

13. The electrode of claim 12, wherein said amplifier, telemetric circuit, and transmitter are located in the interior of said electrode body.

14. The electrode of claim 13, wherein said electrode is adapted to transmit information to a receiver wirelessly.

15. The electrode of claim 1, wherein said electrode body comprises:
   a first portion in the form of a cylinder that includes said teeth on a proximal end of said first portion;
   a second portion that is distal to said first portion, said second portion comprising a constraining wall, said constraining wall including an alignment notch along its outside face, wherein a distal aspect of said first portion is adapted to fit snugly over a proximal aspect of said second portion to the level of said alignment notch.

16. An array of electrodes according to claim 1, wherein said electrodes are interconnected via wire leads, wherein said wire leads are adapted to transfer data and power from one electrode to another.

17. The array of claim 16, wherein said wire leads are further adapted to act as an RF antenna for the transmission of data from said array of electrodes to a receiving computer.

18. The array of claim 16, wherein said array includes a central electrode that includes an electronic component selected from the group consisting of power switch, an infrared light emitter, and gain control.

* * * * *